United States Patent [19]

Bowlin et al.

[11] Patent Number: 5,719,193
[45] Date of Patent: Feb. 17, 1998

[54] METHOD OF POTENTIATING CELL-MEDIATED IMMUNITY UTILIZING POLYAMINE DERIVATIVES

[75] Inventors: Terry L. Bowlin, Maineville; Nellikunja J. Prakash, Cincinnati, both of Ohio

[73] Assignee: Merrell Pharmaceuticals, Inc., Cincinnati, Ohio

[21] Appl. No.: 422,751

[22] Filed: Apr. 14, 1995

Related U.S. Application Data

[63] Continuation of Ser. No. 131,878, Oct. 5, 1993, abandoned, which is a continuation of Ser. No. 995,307, Dec. 22, 1992, abandoned, which is a continuation of Ser. No. 856,818, Mar. 24, 1992, abandoned, which is a continuation-in-part of Ser. No. 708,126, May 29, 1991, abandoned, which is a continuation of Ser. No. 560,453, Jul. 24, 1990, abandoned, which is a continuation of Ser. No. 355,736, May 23, 1989, abandoned.

[51] Int. Cl.⁶ .................................................. A61K 31/13
[52] U.S. Cl. ........................... 514/673; 514/674; 514/885
[58] Field of Search ................................. 514/673, 674, 514/885, 400

[56] References Cited

U.S. PATENT DOCUMENTS

| | | | |
|---|---|---|---|
| 3,947,593 | 3/1976 | Shemano | 514/411 |
| 4,211,794 | 7/1980 | Kraska et al. | 514/674 |
| 4,551,550 | 11/1985 | Bey | 564/215 |
| 4,559,362 | 12/1985 | Umezawa et al. | 514/674 |
| 4,559,367 | 12/1985 | Umezawa et al. | 514/674 |
| 5,109,024 | 4/1992 | Prakash | 514/674 |

FOREIGN PATENT DOCUMENTS

| | | |
|---|---|---|
| 0162413 | 5/1985 | European Pat. Off. . |
| 0378146 | 7/1990 | European Pat. Off. . |

OTHER PUBLICATIONS

Cohen et al Interferon 2. Academic Press. 1980, pp. 83–84.

Ashman in Fundamental of Immunol. Raven Press 1986 p. 289.

Prakash et al Proc. 18th Annual Meeting of AACR 30, p. 585, 1989.

Lymphokines, cytokines and interferon(s). S. Cohen et al in Interferon 2. Academin Press, 1980. pp. 83–84 Ion Gresser, Editor.

Lymphocyte activation, R.F. Ashman in Fundamental Immunology. W.E. Paul. Editor. Raven press. 1986. p. 289.

Terry L. Bowlin et al., Cancer Research 51, pp. 62–66 (1991).

Hamao Umezawa et al., Cancer Research 47, pp. 3062–3065 (1987).

Bowlin et al., *Cancer Research* 46, 5494–5498, Nov. 1986. *Proceedings for the Eightieth Annual Meeting of the American Association for Cancer Research*, vol. 30, p. 585, Mar. 1989.

*Primary Examiner*—Gollamudi S. Kishore
*Attorney, Agent, or Firm*—T. Helen Payne

[57] ABSTRACT

This invention relates to a method of potentiating cell-mediated immunity which comprises administering to a patient a cell-mediated immunity potentiating amount of a compound of the formula:

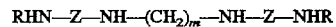

or a pharmaceutically acceptable salt thereof, wherein m is an integer 3 to 12, Z is a saturated $C_2$–$C_6$ alkylene moiety of straight or branched chain configuration, each R group is independently H, a $C_1$–$C_6$ saturated or unsaturated hydrocarbyl, or —$(CH_2)_x$—(Ar)—X wherein X is H, $C_1$–$C_6$ alkoxy, halogen, $C_1$–$C_4$ alkyl, or —$S(O)_xR_1$, x is an integer 0, 1 or 2; and $R_1$ is $C_1$–$C_6$ alkyl.

32 Claims, 1 Drawing Sheet

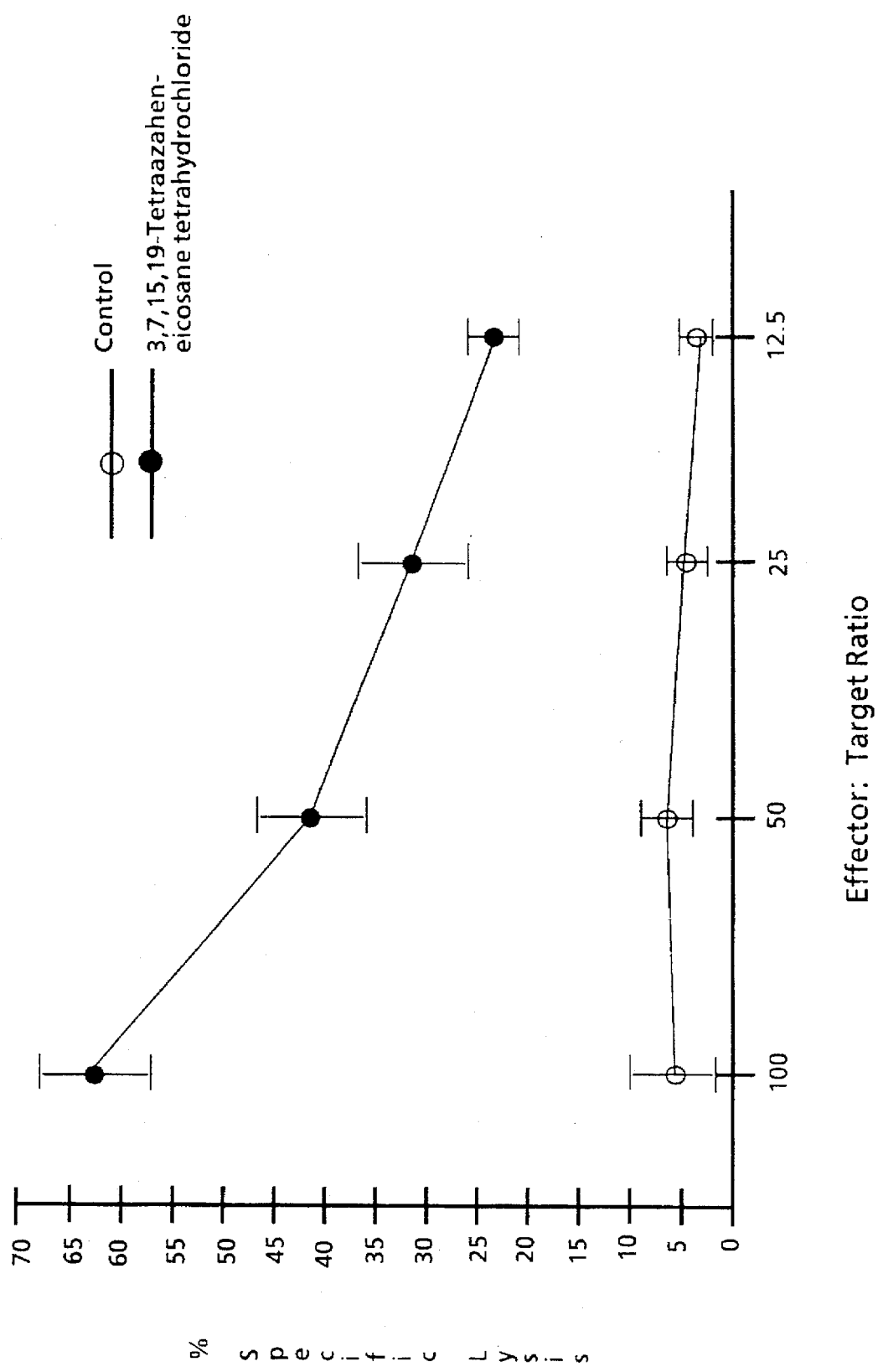

METHOD OF POTENTIATING CELL-MEDIATED IMMUNITY UTILIZING POLYAMINE DERIVATIVES

CROSS-REFERENCE TO RELATED APPLICATION

This is a continuation of application Ser. No. 08/131,878, filed Oct. 5, 1993, now abandoned, which is a continuation of Ser. No. 07/995,307 filed Dec. 22, 1992, now abandoned, which is a continuation of Ser. No. 07/856,818, filed Mar. 24, 1992, now abandoned, which is a continuation-in-part of application Ser. No. 07/708,126, filed May 29, 1991, now abandoned, which is a continuation of application Ser. No. 07/560,453, filed Jul. 24, 1990, now abandoned, which is a continuation of application Ser. No. 07/355,736, filed May 23, 1989, now abandoned, which is herein incorporated by reference.

BACKGROUND OF THE INVENTION

The immune system is composed of two components, a humoral component and a cellular component. The humoral component consists of antibodies, or immunoglobulins, and defends primarily against bacteria and toxic molecules. The cellular component, or cell-mediated immunity, comprises specific and nonspecific cytotoxic effector cells, including T-cells, natural cell-mediated cytotoxic cells, and macrophages. T-cells, or T-lymphocytes, have no detectable spontaneous immunologic activity. Rather, they are activiated and react upon exposure to specific target cells, known as antigens, following sensitization. In contrast, natural cell-mediated cytotoxic cells demonstrate spontaneous nonspecific cytotoxic reactivity towards target cells without prior sensitization. Two distinct, although probably related, natural cell-mediated cytotoxic cell subpopulations exist. They were originally defined based primarily upon target cell susceptibility, and include natural killer (NK) cells and natural cytotoxic (NC) cells. Macrophages, or monocytes, can also have spontaneous cytotoxicity reactivity toward target cells. It has now been found that certain polyamine derivatives potentiate cell-mediated immunity.

BRIEF DESCRIPTION OF THE DRAWINGS

FIG. 1 depicts cell-mediated immunity assessed on day 7 of YAC-1 tumor target cells. Cytoxicity is expressed as the percentage of specific lysis versus the effector to target cell ratio. The ○ represents control; the ● represents 3,7,15,19-tetraazaheneicosane tetrahydrochloride.

DETAILED DESCRIPTION OF THE INVENTION

The present invention relates to a method of use of certain polyamine derivatives to potentiate cell-mediated immunity. More specifically, this invention relates to a method of potentiating cell-mediated immunity which comprises administering to a patient in need thereof an effective cell-mediated immunity potentiating amount of a compound of formula [I]

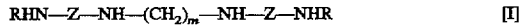

$$RHN-Z-NH-(CH_2)_m-NH-Z-NHR \qquad [I]$$

or a pharmaceutically acceptable salt thereof, wherein m is an integer 3 to 12, Z is a saturated $C_2$–$C_6$ alkylene moiety of straight or branched chain configuration, each R group is independently H, a $C_1$–$C_6$ saturated or unsaturated hydrocarbyl, or —$(CH_2)_x$—(Ar)—X wherein Ar is phenyl or naphthyl, X is H, $C_1$–$C_6$ alkoxy, halogen, $C_1$–$C_4$ alkyl, —$S(O)_xR_1$, wherein x is an integer 0, 1, or 2, and $R_1$ is $C_1$–$C_6$ alkyl.

In those instances wherein R is a saturated hydrocarbyl moiety, such compounds include straight, branched, or cyclized hydrocarbyl moieties. When R is an unsaturated hydrocarbyl moiety, such moieties include those moities having one or two double bonds, and those having one triple bond which may be represented by moieties such as —$CH_2CH=CH_2$, —$CH_2CH_2CH=CH_2$, —$CH_2CH=CH$, and —$CH_2CH=C=CH_2$. In those instances defined by the moiety Z, such moiety includes straight and branched alkyl moieties having from two to six carbon atoms. In those instances defined by the $(CH_2)_m$ moiety, such moieties include straight and branched alkylene moieties having from 3 to 12 carbon atoms.

Compounds of the above formula can be used according to the present invention as pharmaceutically acceptable acid addition salts. The term "pharmaceutically acceptable acid addition salt" encompasses both organic and inorganic acid addition salts including, for example, those prepared from acids such as hydrochloric, hydrofluoric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, napthalenesulfonic, propionic, and the like. The hydrochloric acid addition salts are preferred. The selection and preparation of pharmaceutically acceptable non-toxic acid addition salts are within the ability of one of ordinary skill in the art utilizing procedures and techniques well known and appreciated in the art.

As used herein, the term "patient" refers to a warm-blooded animal, such as a mammal. It is understood that dogs, cats, rats, mice horses, bovine cattle, sheep, and humans are examples within the scope of the meaning of the term.

Treatment of a patient comprises administering to said patient an amount of a compound of formula [I] which potentiates cell mediated immunity. In effecting treatment of a patient, a compound of formula [I] can be administered parenterally in any manner which makes the compound bioavailable in effective amounts, including for example, by intraperitoneal (i.p.), subcutaneous (s.c.), intranasal, intrarectal, or intravenous (i.v.) injection. Administration by i.v. injection is preferred.

An effective cell mediated immunity potentiating amount and an effective effector cell potentiating amount of a compound of formula [I] is that amount which upon administration to a patient in single or multiple doses is effective in potentiating cell mediated immunity and one or more effector cells.

The polyamine derivatives of formula [I] potentiate cell-mediated immunity by potentiating the activity of effector cells comprising the cellular component of the immune system. Examples of these effector cells include T-cells or T-lymphocytes, natural cell-mediated cytotoxic cells such as natural killer cells and natural cytotoxic cells, and macrophages or monocytes. These effector cells exhibit cytolytic activity against a wide variety of target cells, including neoplasms, and cells infected or invaded by viruses, or foreign or non-foreign agents. Accordingly, the polyamine derivatives of formula [I] are useful wherein it is desired to potentiate a patient's cell-mediated immunologic response to target cells. Such instances include, for example, treating neoplastic and viral disease states.

The term "neoplastic disease" as used herein refers to an abnormal state or condition characterized by rapidly proliferating cell growth or a neoplasm such as a carcinoma, a sarcoma, a leukemia, and a melanoma. Such neoplastic diseases include: leukemias, including but not limited to acute lymphoblastic, chronic lymphocytic, acute myloblastic and chronic mylocytic; carcinomas, including but not limited to those of the cervix, esophagus, stomach, kidneys, liver, small intestines, colon, and lungs; sarcomas, including but not limited to osteosarcoma, lipoma, liposarcoma, oesteroma, hemangioma, and hemangiosarcoma; melanomas, including amelanotic and melanotic; and mixed types of neoplasias such as, for example, carcinosarcoma, lymphoid tissue type, folicullar reticulum cell sarcoma, and Hodgkins Disease. As used herein, "treating neoplastic disease states refers to slowing, interrupting, arresting or stopping its growth and metastases, and does not necessarily indicate a total elimination of the neoplasm. It is believed that prolonging the survivability of a patient, beyond being a significant advantageous effect in and of itself, also indicates that the growth of the neoplasm has been controlled.

The term "viral disease" as used herein refers to an abnormal state or condition characterized by viral transformation of cells, viral replication, and proliferation, such as the lack of independent metabolism, the ability to replicate only within living host cells, the ability to reproduce with genetic continuity, and the possibility of mutation. Such viral diseases or infections include: retroviruses, including but not limited to HTLV-I, HTLV-II, human immunodeficiency viruses, HTLV-III (AIDS virus), and the like; RNA viruses, including but not limited to influenza type A, B, and C, mumps, measles, rhinovirus, dengue, rubella, rabies, hepatitis virus A, encephalitis virus, and the like; and DNA viruses, including but not limited to herpes, vaccinia, pappiloma virus (wart), hepatitis virus B, and the like. As used herein, "Treating viral disease states" refers to slowing, interrupting, arresting, or stopping the viral transformation of cells or the replication and proliferation of the virus, and does not necessarily indicate total elimination of the virus.

An effective dose or amount of the compound of formula [I] can readily be determined by the attending diagnostician and is a function of a number of factors including, but not limited to, the species of mammal, its size, age, and general health, the disease state involved, the compound selected, the mode of administration, the bioavailability characteristics of the preparation administered, the dose regimen selected, and the use of concomitant medication or therapy. The correct amount for any specific situation can be readily determined by those skilled in the art using conventional range finding techniques and analogous results observed under other circumstances. An effective amount will vary from about 1 milligram per kilogram of body weight per day (mg/kg/d) to about 500 mg/kg/d, and preferably will be about 5 mg/kg/d to about 50 mg/kg/d.

The compounds of formula [I] may be embodied in pharmaceutical compositions for parenteral administation. These pharmaceutical compositions comprise a cell-mediated immunity potentiating amount of one or more compounds of formula [I] in an admixture with one or more pharmaceutically acceptable excipients. Such compositions are prepared in a conventional manner well known in the art of pharmaceutical preparations. The amounts of the active ingredient(s) in a unit dosage form and the dosage regimen are adjusted to provide a sustained pharmacologic effect at the dosage regimen selected.

Pharmaceutically acceptable excipients are substances that are chemically inert to the active compound(s) and have no detrimental side effects or toxicity to mammals under the conditions of use. Suitable excipients include solvents, such as water, alcohol, and propylene glycol, surface active agents, lubricants, flavors, colorants, and the like. Such carriers and excipients are known to those in the art and are disclosed, for example, in texts such as *Remington's Pharmaceutical Sciences*, 15th Edition, Mack Publishing Company, Easton, Pa., (1975).

Injectable dosage forms of a solution or suspension of formula [I] can be prepared, for example, in a physiologically-acceptable diluent with a pharmaceutical carrier which can be a sterile liquid such as water and oils with or without the addition of a surfactant and other pharmaceutically-acceptable adjuvants. Illustrative of oils which can be employed in these preparations are those of petroleum, animal, vegetable, or synthetic origin, including for example, peanut oil, soybean oil, and mineral oil. In general, water, saline, aqueous dextrose, and related sugar solution ethanols and glycols such as propylene glycol or polyethylene glycol are preferred liquid carriers, particularly for injectable solutions.

In general, the compounds of formula [I] may be prepared by chemical reactions analogously known in the art, such as that described in pending U.S. patent application Ser. No. 295617, filed Jan. 10, 1989, and pending U.S. patent application Ser. No. 295721, filed Jan. 10, 1989, both incorporated herein by reference. The choice of any specific route of preparation is dependent upon a variety of factors. For example, general availability and cost of reactants, applicability of certain generalized reactions to specific compounds, and so forth, are all factors which are fully understood by those of ordinary skill in the art and all contribute to the choice of synthesis in the preparation of any specific compound embraced formula [I].

With the foregoing in mind, the following reaction schemes are illustrative of the pathways by which the compounds of formula [I] utilized by the present invention may be made.

A preferred route for the synthesis of compounds of formula [I] wherein Z is —$CH_2CH_2CH_2$—, but also applicable by analogy for other compounds of formula [I] wherein Z is an alkyl substituted propylene group, such as for example —$CH(CH_3)CH_2CH_2$—, is presented by Reaction Scheme A.

REACTION SCHEME A $H_2N(CH_2)_mNH_2$

[1a] + $\xrightarrow{\text{EtOH}}$ $NC(CH_2)_2NH(CH_2)_mNH(CH_2)_2CN$ $H_2C=CHCN$ [2]

[2] + $H_2$ $\xrightarrow[\text{HCl/AcOH}]{PtO_2}$ $H_2N(CH_2)_3NH(CH_2)_mNH(CH_2)_3NH_2 \cdot 4\,HCl$

[3]

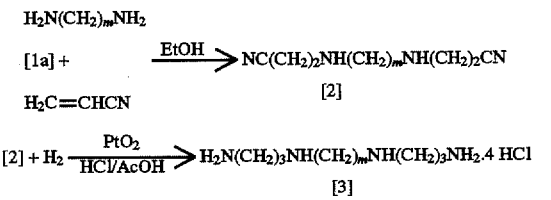

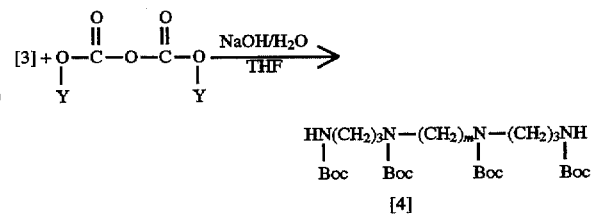

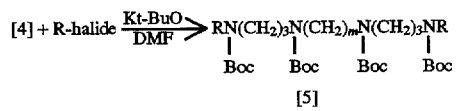

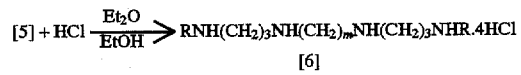

wherein m and R are defined in formula [I] except that when R is X—(Ar)—$(CH_2)_x$, x cannot be zero, Boc is the t-butoxycarbonyl protecting group, and Y is the tert-butyl group.

The initial step of this process entails an N-alkylation of the appropriate diamine [1a] with 2 equivalents of acrylonitrile by heating the reactants, either in a suitable solvent or neat, according to standard conditions well known in the art. The resulting cyano derivatives [2] are chemically reduced by reaction with hydrogen in the presence of a catalyst ($PtO_2$) in a suitable solvent, such as acetic acid containing 8 equivalents of hydrochloric or hydrobromic acid, to produce the resulting hydrohalic salts [3] according to standard procedures well known in the art. Of course, other reducing systems, e.g., reduction with lithium aluminum hydride, may also be utilized to produce compounds of formula [3]. Following the preparation of these compounds the hydrohalic salts are neutralized with base and the nitrogen atoms are protected, preferably with di-t-butyldicarbonate according to standard operating conditions well known in the art. The tetra N-protected amines [4] are alkylated by reacting [4] with the appropriate alkyl halides (chloro or bromo) in the presence of potassium butoxide according to standard alkylation procedures well known in the art. When it is desired to provide compounds of the general formula above wherein both R groups are the same, about 3 equivalents of the alkyl halide is reacted. When it is desired to provide compounds of the general formula above wherein the R groups are not the same, monosubstitution of compounds of formula [4] is effected by reacting about 1 to about 1.5 equivalents of the alkyl halide with subsequent isolation of the mono-substituted compound according to standard procedures well known in the art and optionally further reacting the monosubstituted compound with the desired different alkyl halide. Following alkylation the N-protective groups of compound [5] are removed by standard procedures, e.g., treatment with acid, preferably HCl, in the presence of a suitable solvent system, e.g., diethyloxide in ethanol, to obtain the desired products [6].

Alternatively, compounds of formula [3] and their otherwise prepared homologs may be subjected to a reductive alkylation using an appropriate aldehyde. The reduction is effected by hydrogenation in the presence of $PtO_2$ or sodium cyanoborohydride according to well known procedures. This procedure does not require protection of the nitrogen atoms of the intermediates.

A preferred route for the preparation of compounds of formula [I] wherein Z is —$CH_2(CH_2)_2CH_2$—, but which is also applicable by analogy to those compounds wherein Z is any straight chain, is presented in Reaction Scheme B.

REACTION SCHEME B

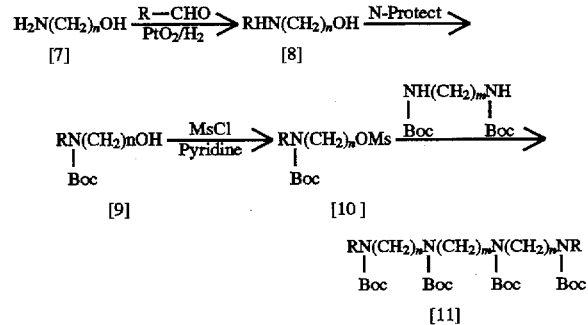

wherein m and R are defined in formula [I], n is an integer 2 to 6 describing a straight chain alkylene moiety, Boc is the t-butoxycarbonyl protecting group, and Ms is mesyl.

This synthesis is initiated by reductive techniques well known in the art using an amino alcohol [7] and an appropriate aldehyde to form R-substituted amino alcohols [8]. The nitrogen atom is protected, preferable with di-t-butyldicarbonate according to standard operating conditions well known in the art to yield the N-protected amino alcohols [9] which are converted to their mesylates [10] by known reaction conditions, e.g., reation with mesylchloride in the presence of pyridine, preferably in a solvent such as $CH_2Cl_2$. The mesylate is subjected to alkylation with an N-protected diamine (i.e., $BocNH(CH_2)_mNHBoc$) in the presence of potassium t-butoxide in a solvent such as DMF. The so-produced tetra N-protected tetramines [11] are deprotected as in Scheme A. In essence, the foregoing reductive alkylation, N-protection, mesylation, alkylation, and deprotection procedures all employ techniques and reaction conditions which are well known in the art.

In those instances wherein Z is a saturated ($C_2$–$C_6$) branched chain alkylene moiety, those compounds may be prepared in an analogous manner described in Reaction Scheme C.

REACTION SCHEME C

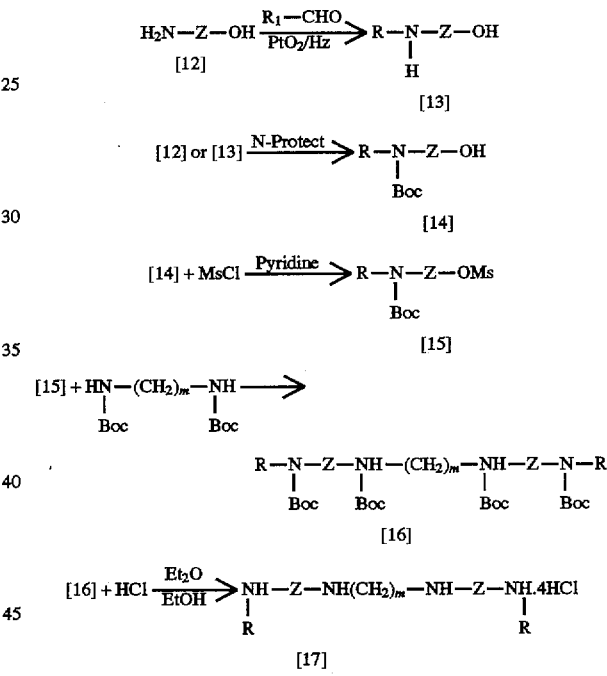

wherein m, R, and Z are defined in formula [I], and $R_1$ is H, methyl, or ethyl.

The appropriate primary amino alcohol [12] containing a branched chain hydrocarbylene moiety, i.e., Z, is prepared by standard procedures well known in the art. If desired, the primary amine can at this point be converted to a secondary amine [13], by a reductive alkylation with the appropriate aldehyde. The amino alcohol is reacted as described in Reaction Scheme A by standard conditions well known in the art to effect protection of the amines with an appropriate N-protecting group such as Boc [14]. The mesylates of the N-protected amino alcohols [15] are prepared and are alkylated with the appropriate N-protected diamine, i.e., BocNH$(CH_2)_m$NHBoc, using standard procedures well known in the art as discussed for Reaction Scheme B. The so-produced tetra N-protected tetramines [16] are deprotected as in Reaction Scheme A to yield compounds of the formula [I]. In essence, the foregoing reductive alkylation, N-protection, mesylation, alkylation, and deprotective procedures all employ techniques and reaction conditions which are well known in the art.

Where it is desired to provide a compound of formula [I] wherein each R group is not the same, the substituted mesylates are prepared separately and monoalkylation of the appropriate N-protected diamine (i.e., BocNH(CH$_2$)$_m$NHBoc) is effected by reacting the diamine with about 1.0 to 1.5 equivalents of one of the mesylates with subsequent isolation of the monosubstituted compound and optionally further reacting the monosubstituted compound with the desired different substituted mesylate.

In those instances in which it is desired to prepare compounds of formula [I] wherein Z is an alkyl-substituted propylene group such as —CH(Q)CH$_2$CH$_2$— wherein Q is a saturated alkyl moiety comprising 1 to 3 carbon atoms of straight or branched chain configuration, Reaction Scheme D can be used to obtain intermediates of formula [22] which can be de-protected to yield primary diamines of formula [23] or which can optionally be subjected to alkylation of the N-terminal groups in a manner analogous to that described in Reaction Scheme A prior to deprotection.

REACTION SCHEME D

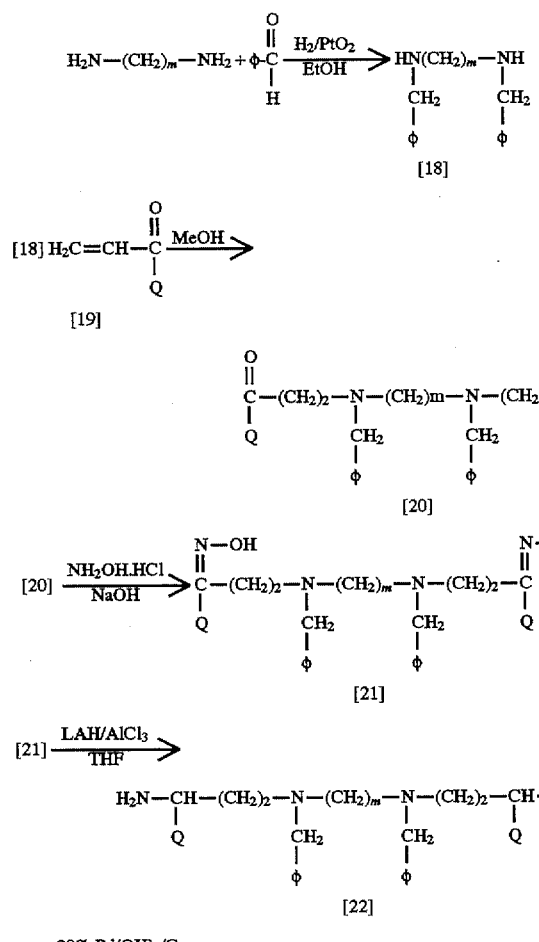

wherein m is defined in formula [I], Ø is phenyl, and Q is as defined above.

The initial step of the process entails a reductive alkylation wherein the appropriate diamine is reacted with hydrogen gas and 2 equivalents of benzaldehyde in the presence of a catalyst such as PtO$_2$ to yield the N-protected diamine [18] under standard conditions well known in the art. The N-protected diamine [18] is then alkylated with 2 equivalents of the appropriate vinyl ketone [19] in a suitable solvent such as methanol using standard techniques. The resulting N-substituted diamine [20] is further reacted under standard conditions with hydroxylamine hydrochloride in the presence of base such as NaOH in a suitable solvent such as ethanol/water. The resulting oximes [21] are reduced to the corresponding N-protected di-primary amines [22] by reaction with lithium aluminum hydride (LAH) in the presence of AlCl$_3$ in a suitable solvent such as THF according to standard procedures. Where the di-primary amine is desired as the final product, the N-protected di-primary amines [22] are deprotected by reaction with hydrogen gas in the presence of a suitable catalyst such as Pearlman's Catalyst (i.e., 20% Pd(OH)$_2$ on carbon) and a suitable solvent such as ethanol according to standard procedures. When secondary amines are desired as the amino-terminal groups of the final product, the N-protected di-primary amines [22] can be further alkylated with an appropriate aldehyde prior to deprotection in a manner analogous to that described for Reaction Scheme A.

In those instances wherein it is desired to prepare compounds of formula [I] wherein Z is —CH$_2$—CH$_2$—, it is preferred to employ Reaction Scheme E to obtain the necessary intermediates [14] which could be subjected to the alkylation procedures discussed above in Scheme A.

REACTION SCHEME E

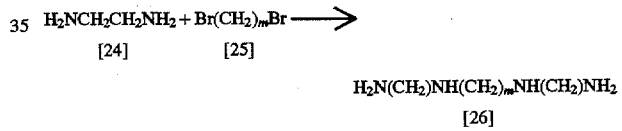

wherein m is as defined in formula [I].

The foregoing N-alkylation entails the reaction of an appropriate dihaloalkane [25] with excess quantities (10×) of ethylene diamine [24] by heating the reactants at reflux temperatures in a suitable solvent, e.g., ethanol. Preparation of the final products bearing the desired R substituents on the terminal nitrogen atoms of the intermediates [26] may be effected by N-protection, alkylation with the appropriate alkyl halide, and deprotection in an analogous manner to that described for Reaction Scheme A. Preferably, the alkylation can be carried out by the reductive alkylation procedures without N-protection as alternatively described for Reaction Scheme A.

A preferred method for preparing compounds of formula [I] wherein —(CH)$_x$—(Ar)—X represents phenethyl or naphthylethyl, particularly wherein Z is C$_3$ and m is 8, is the reaction of an aroylchloride according to the method depicted in Reaction Scheme F.

REACTION SCHEME F

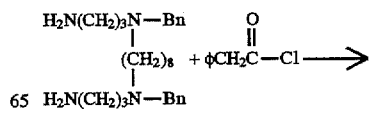

9
-continued
REACTION SCHEME F

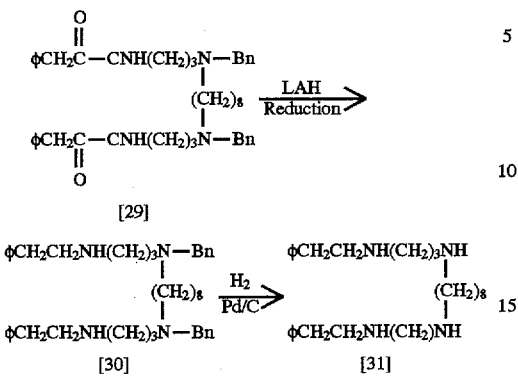

[29]

[30]   [31]

wherein Bn is benzyl, φ is phenyl, and LAH is lithium aluminum hydride.

As stated above, the foregoing reaction is a preferred method for the preparation of one particular compound which entails N-alkylation of a partially protected intermediate [27] with an arylacetyl chloride [28] in the presence of triethylamine, using an inert solvent, to form an amide [29] which is chemically reduced, preferably with LAH, and the resulting product [30] is catalytically de-benzylated ($H_2Pd/C$) to form the desired end product [31]. These steps entail reaction techniques and procedures well known in the art. Of course the same reaction scheme can be applied for the preparation of other compounds of formula [I]; adoption of the technique being with the usual caveats well understood by those of ordinary skill in the art.

In those instances wherein $-(CH)_x-(Ar)-X$ represents an aromatic moiety (X-phenyl or X-naphthyl) which is attached directly to the terminal nitrogen atoms (i.e., x is zero) then such compounds may be prepared according to the general reactions of Reaction Scheme G.

REACTION SCHEME G

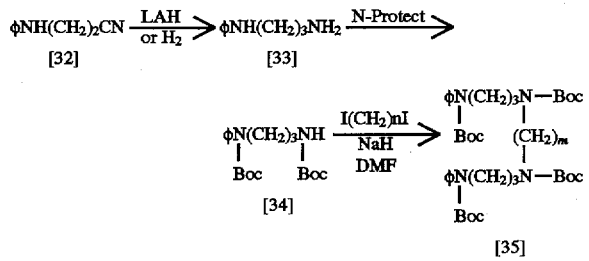

The foregoing reaction scheme depicts the preparation of compounds wherein Ar is phenyl, the first step of which is a LAH reduction effected according to procedures published is the art (Bul. Soc. Chim. Fr., Part 2, 165-7 (1979)). Of course this reaction scheme can be expanded to include napthyl and X-substituted intermediates which will not be adversely affected by the reaction conditions. Preferable the N-protection uses the t-butoxycarbonyl protecting groups which are put on and taken off according to standard techniques already mentioned hereinabove. The N-protected compounds are alkylated by reaction with an appropriate dihaloalkane using standard and well known procedures.

In those instances wherein it is desired to prepare compounds of formula [I] which contain an unsaturated hydrocarbyl moiety, i.e., acetylenic, allenic, or allylic moiety-

containing compounds, it is preferred to use the techniques of Reaction Scheme H.

REACTION SCHEME H

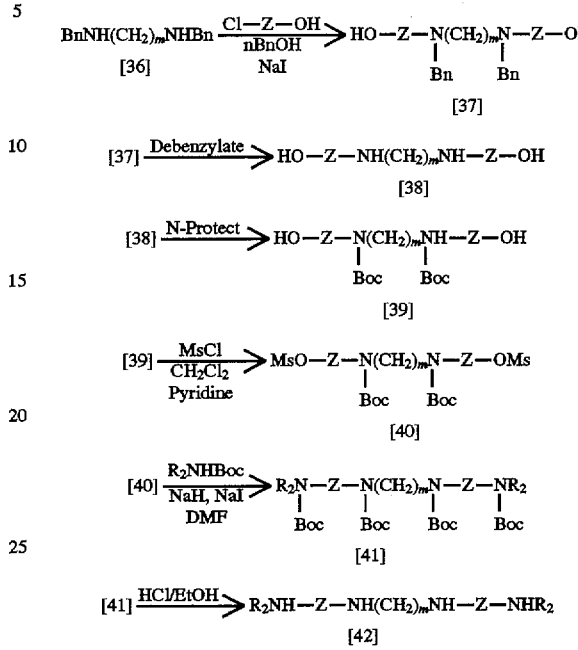

wherein $R_2$ is an appropriate unsaturated hydrocarbyl moiety, Bn is benzyl, MsCl is methanesulfonyl chloride, and Boc is the t-butoxycarbonyl protecting group.

In the foregoing reaction a dibenzylated diamine [36] is N-alkylated by a simple displacement reaction to form compounds [37] which are sequentially benzylated [38] and N-protected. These steps are effected according to well known and standard procedures. The resulting bishydroxyamino-alkanes [39] are mesylated and the mesylates [40] are alkylated with two equivalents of an N-protected amine bearing an appropriate unsaturated hydrocarbyl moiety, e.g., N-(t-butoxycarbonyl)-2,3-butadienylamine. A so-obtained tetra protected tetramine [41] is then readily de-protected to produce the desired compounds [42].

In those instances wherein it is desired to convert an alkylthio substituent to one of its higher oxidation states the alkyl thioether is treated with a peracid according to known conditions. Suitable oxidizing agents are $H_2O_2$ and $NaIO4$, but meta-chloroperoxybenzoic acid is preferred. In effecting the oxidation to a sulfinyl derivative 1 molar equivalent (per alkylthioether moiety) is used and 2 molar equivalents of the peracid will yield the sulfonyl derivatives. The oxidations are effected at temperatures of about 0° C. to room temperature in solvents which themselves are not susceptible to oxidation. Preferred solvents are $CH_2Cl_2$, $CHCl_3$, acetic acid, and ethyl acetate.

As is well known in the art of pharmaceutical inventions wherein generic classes of compounds are involved, certain specific compounds are more effective in their end use applications than other members of the generic class. The following compounds are preferred in the method of use described by the present invention:

1,18-Bis[(phenyl)methyl]-1,5,14,18-tetraazaoctadecane•4HCl, 1,20-Bis[(phenyl)methyl]-1,6,15,20-tetraazaeicosane•4HCl, N,N'-Bis(3-aminobutyl)-1,8-octanediamine, N,N'-Bis(3-ethylamino)butyl]-1,7-diaminoheptane tetrahydrochloride, 1,4,13,16-tetra(t-butoxycarbonyl)-1,4,13,16-tetraazahexadecane, 1,18-Bis[(2-phenyl)ethyl]-1,5,14,18-tetraazaoctadecane•4HCl, 1,18-Bis(phenyl)-1,5,14,18-tetraazaoctadecane, 1,18-Bis(2,3-butadienyl)-1,5,14,18-tetraazaoctadecane tetrahydrochloride.

Especially preferred are the following compounds:

3,7,15,19-tetraazaheneicosane tetrahydrochloride, 3,17-dimethyl-2,6,14,18-tetraazanonadecane tetrahydrochloride, and 4,16-dimethyl-2,6,14,18-tetraazanonadecane tetrahydrochloride.

EXAMPLE 1

1,18-Bis[(phenyl)methyl]1,5,14,18-tetraazaoctadecane•4HCl

Step A: N,N'-Bis-[2,2'-bis(cyano)ethyl]-1,8-diaminooctane

Dissolve 28.8 gm (0.2 mol) of 1,8 diaminooctane in 250 ml of EtOH. Add 27 ml (0.41 mol) of acrylonitrile and gently reflux the mixture overnight. Remove the solvent at reduced pressure. Analysis shows desired material to be >95% pure.

Step B: 1,5,14,18-Tetraazaoctadecane tetrahydrochloride

Combine 50.0 gm of the product of Example 1, 2.0 gm $PtO_2$, 133 ml of conc. HCl at 45 lbs./sq.in. in a shaker flask until hydrogen is no longer taken up. Filter the resulting mixture, evaporate the solvent and triturate the product with 1 liter of EtOH. Filter and dry the product to obtain 51.6 gm of the title compound, Rf is 0.17 (silica gel plates eluted with 40% conc. $NH_3/CH_3OH$).

Step C: 1,5,14,18-Tetra(t-butoxycarbonyl)-1,5,14,18-tetraazaoctadecane

Treat 28.0 gm (0.069 mol) of the product of Step B with 10.99 gm (0.274 mol) of NaOH in 120 ml $H_2O$. When a homogenous solution is obtained add 65.7 gm (0.307 mol) of di-t-butyldicarbonate in 750 ml of THF and stir the resulting mixture for 16 hours. Separate the layers, remove and wash (2×) the aqueous layer with 500 ml $CH_2Cl_2$. Combine and dry ($MgSO_4$) the organics, filter and evaporate (in vacuo) the solvents and flash chromatograph the residue (silica gel), eluting with 25% EtOAc/hexane to yield 30.2 g of the desired product. Rf is 0.33 on silica gel plates eluted with 25% EtOAc/hexane).

Step D: 1,18,-Bis[(phenyl)methyl]-1,5,14,18-tetra(t-butoxycarbonyl)-1,5,14,18-tetraazaoctadecane Dissolve 20.0 gm (0.03 mol) of the product from Step C in 30 ml DMF and treat with 7.5 gm (0.067 mol) KtBuO and 7.96 ml (0.067 mol) BnBr, with stirring for 18 hours. Evaporate the volatiles (0.5 mm and 45° C.) and take up the resulting residue in 1400 ml of EtOAc and water-wash (2×, 500 ml). The organic layer is then dried ($MgSO_4$) and the solvent is evaporated (in vacuo). Flash chromatography on silica gel eluted with 20% EtOAc/hexane yields 12.4 gm (50%) of desired product as a clear viscous oil. Rf is 0.42 (silica gel plates eluted with 25% EtOAc/hexane).

Step E: 1,18-Bis-[(phenyl)methyl]-1,5,14,18-tetraazaoctadecane•4HCl

Dissolve 12.4 g (0.0147 mol) of the product of Step D in 14.7 ml of anhydrous EtOH and treat with 160 ml of 2N HCl in $Et_2O$ with stirring overnight. Filter, wash the filter cake with $Et_2O$, and dry to obtain 7.2 gm of the desired compound, mp >300° C. Rf is 0.24 (from silica gel eluted with 10% conc. $NH_3/CH_3OH$).

EXAMPLE 2

1,20-Bis[(pheny)methyl]-1,6,15,20-tetraazaeicosane•4HCl

Step A: N,N'-Bis(t-butoxycarbonyl)-1,8-octanediamine

Dissolve 10.8 gm (0.075) of diaminooctane in 200 ml $CH_2Cl_2$ and 100 ml $CH_3OH$, add 32.7 gm (0.156 mol) of di-t-butyldicarbonate and stir the mixture overnight. Evaporate, in vacuo, and crystallize the residue from hexane to obtain 20.2 gm of the desired compound, mp 96°–97° C.

Step B: 4-[[(Phenyl)methyl]amino]-butan-1-ol

Combine 4-amino-butan-1-ol (8.9 gm-0.1 mol), benzaldehyde (10.6 gm-0.1 mol), EtOH (100 ml) and $PtO_2$ (0.3 gm), and hydrogenate the mixture at 45 lbs./sq.in. until $H_2$ is no longer taken up. Filter, evaporate the solvent (in vacuo) to yield 17.7 gm of the desired compound. Rf is 0.70 (eluted from silica gel with 10% conc. $NH_3/CH_3OH$).

Step C: 4-[N-(t-butoxycarbonyl)-N-[(phenyl)methyl]amino]butan-1-ol

Combine the butanol of Step B (17.7 g-0.1 mol) and di-t-butyldicarbonate in 100 ml of $CH_2Cl_2$ and stir the mixture overnight. Evaporate off the solvents, in vacuo, and flash chromatograph the residue, eluting from silica gel with 25% EtOAc/hexane to obtain the desired compound. Rf is 0.27 (silica gel plates eluted with 20% EtOAc/hexane).

Step D: 4-[N-(t-butoxycarbonyl)-N-[(phenyl)methyl]amino]-1-methansulfonyl butane Cool (ice-bath) a mixture containing the product of Step C (21.8 gm-0.078 mol), 250 ml $CH_2Cl_2$ and 9.7 ml pyridine (0.12 mol), add in a dropwise fashion (20 minutes) mesylchloride (6.65 ml-0.086 mol) in 6.6 ml $CH_2Cl_2$ and allow the mixture to warm to room temperature, stirring the mixture for 2 hours. Pour the resulting mixture into 200 ml $CH_2Cl_2$, wash with 500 ml 0.5N HCl, saturated $NaHCO_3$, dry over $MgSO_4$, evaporate (in vacuo) and flash chromatograph eluting from the silica gel with 25% EtOAc/hexane to obtain 10.7 g of desired product, Rf is 0.36 (silica gel plates eluted with 25% EtOAc/hexane).

Step E: 1,20-Bis[(phenyl)methyl]-1,6,15,20-tetra-(t-butoxycarbonyl)-1,6,15,20-tetraazaeicosane Admix the products of Step A (5.16 gm-0.015 mol) and of Step D of this example (10.7 g-0.032 mol), Kt-BuO (3.92 gm), NaI (0.2 gm), and 60 ml DMF and stir the mixture for 72 hours at room temperature. Evaporate off the solvent (in vacuo), take up the residue in 600 ml EtOAc and wash (2×) with 200 ml water. Dry the organic layer ($MgSO_4$), evaporate the solvents, and flash chromatograph the viscous residue on silica gel eluting with 20% EtOAc/hexane to obtain the desired product, Rf is 0.22 (silica gel plates eluted with 20% EtOAc/hexane).

Step F: 1,20-Bis[(phenyl)methyl]-1,6,15,20-tetraeicosane•4 HCl

Dissolve the product of Step E (4.7 gm) (0.0054 mol) in 5 ml EtOH and treat with 54 ml of 2N HCl in $EtO_2$, stir the mixture overnight, filter and recrystallize to so-obtained solids from isopropanol/water. Cool, filter and dry the desired product, mp >300° C., Rf is 0.47 (eluted from silica with 10% conc. $NH_3/CH_3OH$).

EXAMPLE 3

N,N'-Bis(3-aminobutyl)-1,8-Octanediamine

Step A: N,N'-Bis((phenyl)methyl)-1,8-octanediamine

Combine 14.4 g (0.1 mol) of 1,8-octanediamine, 20.3 ml (0.2 mol) of benzaldehyde, 0.3 g $PtO_2$ and 150 ml ethanol and treat the mixture with $H_2$ at 45 lb/in² in a shaker flask until no more gas is taken up. Remove the catalyst by filtration and remove the solvent at reduced pressure to yield the title compound.

Step B: N,N'Bis((3-oxo)butyl)-N,N'-bis((phenyl)methyl)-1, 8-octanediamine

Dissolve the product obtained in Step A in 1400 ml of methanol and introduce 21.6 of methyl vinyl ketone on a stream of $N_2$ gas. Stir for 16 hours to yield the title compound.

Step C: N,N'-Bis((3-hydroxyimino)butyl)-N,N'-Bis-((phenyl)methyl)-1,8-octanediamine Combine 18.07 g hydroxylamine hydrochloride, 10.4 g of NaOH and 40 ml of $H_2O$ and add to the solution obtained in Step B. Reflux the mixture for 3 hours, then cool and evaporate the solvent. Pour the reaction mixture into 300 ml of ethyl acetate and wash with 300 ml $H_2O$. Wash the aqueous layer with 300 ml of ethyl acetate (2×). Combine the organic layers and dry over anhydrous $MgSO_4$. Remove the solvent at reduced pressure. Purify the product by flash chromatography (silica gel), eluting with ethyl acetate to yield 34.8 g of the title compound ($R_f$ is 0.42 for TLC on silica gel developed with ethyl acetate).

Step D: N,N'-Bis((3-amino)butyl)-N,N'-Bis((phenyl)-methyl)-1,8-octanediamine

Add 34.8 g of the product of Step C in 100 ml THF to 12.10 g (0.310 mol) of lithium aluminum hydride in 540 ml THF and reflux the mixture while stirring overnight. Cool the mixture and slowly add 15 ml $H_2O$ followed by 45 ml 1N NaOH and stir the mixture for 6 hours. Filter the mixture to remove a white granular precipitate and remove the solvent at reduced pressure. Subject the residue to short path distillation to yield 17.0 g of the title compound (bp 230°–235° C. at 0.1 mmHg).

Step E: N,N'-Bis((3-amino)butyl)-1,8-octanediamine

Combine 5.0 g (0.01 mol) of the product of Step D, 0.5 g of 20% $Pd(OH)_2$ on carbon (Pearlman's Catalyst), and 50 ml of ethanol and treat the mixture with $H_2$ at 45 lb/in² in a shaker flask until no more gas is taken up. Remove the catalyst by filtration and remove the solvent at reduced pressure. Subject the residue to short path distillation to yield 1.59 g of the title compound (bp 145°–148° C. at 0.012 mmHg).

EXAMPLE 4

N,N'-Bis[3-(methylamino)butyl]-1,7-diaminoheptane tetrahydrochloride

Step A: N,N'-Bis[(phenyl)methyl]-1,7-heptanediamine

Combine 1,7-diaminoheptane (65.0 g, 0.5 mol), benzaldehyde (106 gm, 1 mol) and platinum oxide ($PtO_2$)[2.0 g] in ethanol (800 ml) and treat the mixture with hydrogen gas (45 lb/in²) until the uptake of gas ceases. Remove the catalyst by filtration and remove the solvent in vacuo. Purify the residue by bulb to bulb distillation to yield 99.4 g of the title compound (bp 191°–195° C. @ 1.0 mm/Hg).

Step B: N,N'-Bis[(3-oxo)butyl]-N,N'-bis[(phenyl)methyl]-1, 7-diaminoheptane

Dissolve N,N'-bis[(phenyl)methyl]-1,7-heptanediamine (9.3 g, 0.03 mol) in methanol (120 ml) and while stirring the mixture introduce methyl vinyl ketone (5.6 ml, 0.066 mol) in a stream of nitrogen gas. Stir the mixture for 18 hours to yield the title compound.

Step C: N,N'-Bis[(3-hydroxyimino)butyl]-N,N'-bis[(phenyl)methyl]-1,7-diaminoheptane Cool the reaction mixture obtained in step B to 0° C. and to this mixture add a solution of hydroxylamine hydrochloride (4.38 g, 0.063 mol) and sodium bicarbonate (5.54 g, 0.066 mol) in water (40 ml). Stir the mixture at 0° C. for 30 minutes and then stir at ambient temperature for 2 hours. Remove the solvent in vacuo and partition the residue between water (200 ml) and dichloromethane (200 ml). Wash the aqueous layer 3 times with 200 ml of dichloromethane each time. Combine the organic layers and dry over anhydrous $MgSO_4$. Remove the solvent in vacuo to yield 14.4 g of the title compound. Rf is 0.53 for TLC on silica gel developed with ethyl acetate.

Step D: N,N'-Bis[3-(amino)butyl]-N,N'-bis[(phenyl)methyl]-1,7-diaminoheptane

Add a solution of N,N'-bis[(3-hydroxyimino)butyl]-N,N'-bis[(phenyl)methyl]-1,7-diaminoheptane (14.4 g, 0.03 mol) in THF (70 ml) to a mixture of lithium aluminum hydride (5.8 g, 0.15 mol) in THF (250 ml) and reflux the mixture overnight. Cool the mixture and quench slowly with water (5.8 ml), followed by 15% NaOH (5.8 ml), followed by water (17.4 ml). Filter the mixture and wash the filtrate 3 times with 100 ml of THF each time. Combine the organic layers and remove the solvent in vacuo to obtain 13.4 g of the title compound as a clear viscous oil. Rf is 0.33 for TLC on silica gel developed with 4% conc. ammonia in methanol.

Step E: 2,16-Bis(methyl)-1,5,13,17-tetra(t-butoxycarbonyl)-1,5,13,17-tetraazaheptadecane Combine N,N'-bis[3-(amino)butyl]-N,N'-bis[(phenyl)methyl]-1,7-diaminoheptane (13.4 g, 0.029 mol), Pearlman's Catalyst (2.0 g) and ethanol (90 ml) and treat the mixture with hydrogen gas at 45 lb/in² until gas uptake ceases. Remove the catalyst by filtration and remove the solvent in vacuo to obtain 7.7 g of N,N'-bis[3-(amino)butyl]-1,7-diaminoheptane (Rf is 0.37 for TLC on silica gel developed with 40% conc. ammonia in methanol). Dissolve the residue in dichloromethane (90 ml) and treat the mixture with di-t-butyldicarbonate (26.2 g, 0.12 mol) for 3 hours. Remove the solvent in vacuo and purify the residue by flash chromatography on silica gel eluting with 25% ethyl acetate in hexane to yield 17.1 g of the title compound as a clear oil. Rf is 0.35 for TLC on silica gel developed with 25% ethyl acetate in hexane.

Step F: 1,2,16,17-Tetramethyl-1,5,13,17-tetra(t-butoxycarbonyl)-1,5,13,17-tetraazaheptadecane Combine 2,16-bis(methyl)-1,5,13,17-tetra(t-butoxycarbonyl)-1,5,13,17-tetraazaheptadecane (8.5 g, 0.0126 mol) and sodium hydride (60% in oil)[1.21 g, 0.03 mol] in DMF (75 ml) and stir until hydrogen evolution ceases. To this mixture add methyl iodide (1.88 g, 0.03 mol) and stir for 2 hours. Remove the solvent in vacuo and partition the residue between ethyl acetate (400 ml) and water (200 ml). Dry the organic layer over anhydrous $MgSO_4$ and remove the solvent in vacuo. Purify the residue by flash chromatography on silica gel eluting with 22% ethyl acetate in hexane to yield 3.8 g of the title compound as a clear oil. Rf is 0.22 for TLC on silica gel developed with 20% ethyl acetate in hexane.

Step G: N,N'-Bis[3-(methylamino)butyl]-1,7-diaminoheptane tetrahydrochloride

Add 1N HCl in methanol (50 ml) to 1,2,16,17-tetramethyl-1,5,13,17-tetra(t-butoxycarbonyl)-1,5,13,17-tetraazaheptadecane (3.8 g, 0.0054 mol) and stir overnight. Remove the solvent in vacuo and recrystallize the residue two times from methanol/acetonitrile (40/60, v/v) to yield 0.74 g of the title compound as a white solid (mp 238°–9° C.). Rf is 0.31 for TLC on silica gel developed with 40% conc. ammonia in methanol.

EXAMPLE 5

N,N'-Bis[3-(ethylamino)butyl]-1,7-diaminoheptane tetrahydrochloride

Step A: 1,17-Diethyl-2,16-dimethyl-1,5,13,17-tetra(t-butoxycarbonyl)-1,5,13,17-tetraazaheptadecane Combine 2,16-bis(methyl)-1,5,13,17-tetra(t-butoxycarbonyl)-1,5,13,17-tetraazaheptadecane (8.5 g, 0.0126 mol), made as described in Example 5, and sodium hydride (60% in oil)[1.21 g, 0.03 mol] in DMF (75 ml) and stir until hydrogen evolution ceases. To this mixture add ethyl iodide (4.68 g, 0.03 mol) and stir for 2 hours. Remove the solvent in vacuo and partition the residue between ethyl acetate (400 ml) and water (200 ml). Dry the organic layer over anhydrous MgSO4 and remove the solvent in vacuo. Purify the residue by flash chromatography on silica gel eluting with 22% ethyl acetate in hexane to yield 3.9 g of the title compound as a clear oil. Rf is 0.31 for TLC on silica gel developed with 20% ethyl acetate in hexane.

Step B: N,N'-Bis[3-(ethylamino)butyl]-1,7-diaminoheptane tetrahydrochloride

Add 1N HCl in methanol (50 ml) to 1,17-diethyl-2,16-dimethyl-1,5,13,17-tetra(t-butoxycarbonyl)-1,5,13,17-tetraazaheptadecane (3.9 g, 0.0054 mol) and stir overnight. Remove the solvent in vacuo and recrystallize the residue two times from methanol/acetonitrile (40/60, v/v) to yield 0.90 g of the title compound as a white solid (mp 249°–50° C.). Rf is 0.56 for TLC on silica gel developed with 40% conc. ammonia in methanol.

EXAMPLE 6

1,4,13,16-Tetra(t-butoxycarbonyl)-1,4,13,16-tetraazahexadecane

Combine 4.75 gm 1,8-dibromooctane (0.017 mol), 20 ml EtOH and 9.32 ml of ethylene diamine and reflux the mixture overnight. Cool and treat the mixture with 1.4 gm NaOH. Evaporate off the solvent and triturate the residue with $CH_2Cl_2$ (200 ml 2x), filter. Treat the filtrate with 66.6 gm of di-t-butyl-dicarbonate and stir the mixture overnight. Remove the solvent and subject the residue to flash chromatography, eluted with 25% EtOAc/hexane to yield the desired product. Rf is 0.64 eluted from silica gel with 50% EtOAc/hexane.

The foregoing may be bis-N-alkylated and the product deprotected by methods analogous to Steps D and E of Example 1 to produce desired compounds of the Formula R'HN(CH$_2$)$_2$N(CH$_2$)$_8$N(CH$_2$)$_2$NHR', e.g., 1,16-Bis[(phenyl)methyl]-1,4,13,16-tetraazahexadecane•4 HCl.

EXAMPLE 7

1,18-Bis[(2-phenyl)ethyl]-1,5,14,18-tetraazaoctadecane•4HCl

Step A: 1,18-Bis[[(phenyl)methyl]carbonyl]-5,14-bis-[(phenyl)methyl]-1,5,14,18-tetraazaoctadecane Chill a solution of 5,14-bis[(phenyl)methyl]-1,5,14,18-tetraazaoctadecane (2.2 g, 5 mmole) and triethylamine (2 g, 20 mmole) in chloroform (100 ml) in an ice bath. Add a solution of phenylacetyl chloride (2.3 g, 15 mmole) in chloroform (10 ml) dropwise. Remove the ice bath and stir the mixture at ambient temperature for 18 hours. Extract the reaction mixture with aqueous sodium bicarbonate, dry the organic layer and evaporate. Chromatograph the residue on a flash silica gel column (ethyl acetate) to give 3 g of the desired product as a thick oil.

Step B:

Add a solution of the product of Step A in THF (150 ml) dropwise to a suspension of LAH (0.5 g) in THF (500 ml). Stir the mixture for 48 hours at ambient temperature. Decompose the excess reducing agent by dropwise addition of 1 ml of water, 1 ml of 15% NaOH then 3 ml of water. Filter the mixture and evaporate the filtrate. Take the residue up in ethanol (100 ml) and add anhydrous HCl gas to convert the product, 1,18-bis[(phenyl)ethyl]-5,14-bis-[(phenyl)methyl]-1,5,14,18-tetraazaoctadecane, to its tetrahydrochloride salt. Hydrogenate this product in ethanol (150 ml) in the presence of Pearlman's catalyst (0.3 g) at 43 psig on a Parr hydrogenation apparatus for 24 hours. Filter off the catalyst and evaporate the filtrate. Crystallize the residue from 2-propanol to give the product 1,18-bis-[(phenyl)ethyl]-1,5,14,18-tetraazaoctadecane tetrahydrochloride salt hemihydrate, mp 228°–231° C.

EXAMPLE 8

1,18-Bis(phenyl)-1,5,14,18-tetraazaoctadecane

Step A: N-(Phenyl-N,N'-bis(t-butoxycarbonyl) propanediamine

Cool 200 ml of anhydrous $Et_2O$ in an ice bath and add lithium aluminum hydride (8.74 gm-0.23 mol). Add, in a dropwise fashion over 30 minutes, 3-anilinopropionitrile (14.6 gm) in 50 ml of $Et_2O$, remove the ice bath, and reflux the resulting mixture overnight. Sequentially add 8.7 ml of water, 1.5 g of NaOH (in 10 ml of water) and 25 ml of water. Filter the resulting ppt, rinse with 200 ml of $Et_2O$ and remove the solvent, in vacuo, and treat the resulting N-(phenyl) propanediamine with 43.6 g of di-t-butyldicarbonate in 600 ml of $CH_2Cl_2$. After stirring overnight, evaporate off the solvent and subject the residue to flash chromatography from silica gel eluting with 17% EtOAc/hexane to produce the desired compound. Rf is 0.50 (eluted from silica gel with 25% EtOAc/hexane).

Step B: 1,18-Bis(phenyl)-1,5,14,18-tetra(t-butoxycarbonyl)-1,5,14,18-tetraazaoctadecane Stir a mixture containing the product of Step A (13.0 gm), diiodooctane 3.70 gm) and 4.14 g of potassium t-butoxide in 200 ml of DMF for about 16 hours. Evaporate the solvent at 0.5 mm and 45° C., take up the residue in 800 ml of EtOAc. Wash (2x) with 300 ml of water, dry (MgSO$_4$) and remove the solvent in vacuo. Subject the so-obtained viscous oil to flash chromatography, eluting with 15% EtOAc from silica gel to yield 5.7 g of the desired product. Rf of 0.36 (eluted from silica gel with EtOAc/hexane). Remove the N-boc protecting groups according to the procedure of Step E of Example 1 to produce the title compound of this example. mp 264°–267° C.

EXAMPLE 9

1,18-Bis(2,3-butadienyl)-1,5,14,18-tetraazaoctadecane tetrahydrochloride

Step A: N-(t-Butoxycarbonyl)propargylamine

In a dropwise fashion, add propargylamine (25 gm) in 25 ml of $CH_2Cl_2$ to a stirring mixture of di-t-butyldicarbonate (99.18 gm) in 900 ml of $CH_2Cl_2$. After 2 hours, remove the solvent, in vacuo, to obtain 70 gm of the desired N-protected propargylamine.

Step B: N-(t-Butoxycarbonyl)-2,3-butadienylamine

Reflux a mixture containing N-(t-butoxycarbonyl)-propargylamine (70 gm), 93.5 ml of 32% formaldehyde, 76.4 ml of diisopropylamine, 19.66 gm of cuprous bromide and 860 ml of p-dioxane for 12 hours. Cool and dilute the resulting mixture with 3000 ml of Et₂O, wash with 500 ml of water, 1000 ml acetic acid, 500 ml of water (2×), 200 ml sat'd. sodium chloride, dry (MgSO₄) and evaporate in vacuo. Flash chromatograph the residue eluting from silica gel with 10% Et₂O/hexane to yield 40.8 g of the desired compound. Rf is 0.31 (eluted from silica gel with 10% EtOAc/hexane).

Step C: N,N-Bis[(phenyl)methyl]-1,8-diaminooctane

Combine 14.4 gm of diaminooctane, 20.3 ml of benzaldehyde and 0.66 gm of Pt₂O in 100 ml of ethanol. Treat the resulting mixture with hydrogen at 45 lbs./sq.in. until no further hydrogen is taken up. Filter, evaporate the solvent (in vacuo), and distill the rendered material to obtain 25.5 gm of the desired product, bp 185°–190° C. at 0.1 mm.

Step D: 1,18-Bis(hydroxy)-5,14-bis[(phenyl)methyl]5,14-diazaoctadecane

Reflux a mixture containing 25.5 g of the product of Step C, 13.2 ml of 3-chloro-1-hydroxy-propane, 50.4 gm of Na₂CO₃ and 1.19 gm of sodium iodide in 40 ml of n-butanol for 18 hours. Cool the mixture and pour into 700 ml of ethylacetate, wash with water, dry over MgSO₄ and remove the solvent (in vacuo) to obtain a residue which upon distillation yields 30.0 gm of the desired product, bp 250°–252° C. at 0.1 mm.

Step E: 1,18-Bis(hydroxy)-5,14-diazaoctadecane

Hydrogenate a mixture containing 3.0 gm of the product of Step D, 30 ml of AcOH and 0.6 gm of palladium oxide at 45 lbs./sq.in. until no further hydrogen is taken up. Filter and remove the solvent (in vacuo) to yield 1.77 gm of the desired product, Rf is 0.37 (eluted from silica gel with 10% conc. NH₃/CH₃OH).

Step F: 1,18-Bis(hydroxy)-5,14-bis-(t-butoxycarbonyl)-5,14-diazaoctadecane

Stir a mixture containing 1.77 gm of the product of Step E, 2.97 gm (0.0136 mol) of di-t-butyldicarbonate, 3 ml of triethylamine and 50 ml of CH₂Cl₂ overnight. Dilute the mixture with 200 ml of CH₂Cl₂, wash with 200 ml of 0.5N HCl, and then 100 ml of sat'd NaCl, dry (over MgSO₄) and remove the solvent (in vacuo). Flash chromatograph the residue, eluting from silica gel with 75% EtOAc to obtain the desired product, Rf 0.29, (eluted from silica gel with 75% EtOAc/hexane).

Step G: 1,18-Bis(methansulfonyl)-5,14-bis(t-butoxycarbonyl)-5,14-diazaoctadecane Cool to 0° C. a mixture containing 3.0 gm of the product of Step F, 3.3 ml of triethylamine and 70 ml of CH₂Cl₂. In a dropwise fashion add 1.22 ml of mesylchloride in 10 ml of CH₂Cl₂, and stir the resulting mixture at 0° C. for 1½ hours. Pour the mixture into 100 ml of CH₂Cl₂, wash with 200 ml of 1N AcOH, 100 ml of water, 100 ml of sat'd sodium bicarbonate, dry over MgSO₄ and remove the solvent in vacuo. Flash chromatograph the residue, eluting from silica gel with 60% EtOAc/hexane to obtain 3.5 gm of the desired product. Rf is 0.39.

Step H: 1,18-Bis(2,3-butadienyl)-1,5,14,18-tetra-(t-butoxycarbonyl)-1,5,14,18-tetraazaoctadecane Combine a mixture containing 3.5 gm of the product of Step G, 1.74 gm of sodium iodide, 0.51 gm of hexane washed sodium hydride (60% in oil) in 12 ml of DMF with 2.16 gm of N-(t-butoxycarbonyl)-2,3-butandienylamine (i.e., the product of Step B) and allow the resulting mixture to stand for 2 hours. Remove the solvent (in vacuo), add 350 ml of ethyl acetate to the residue, wash with 50 ml of water (4×), 100 ml sat'd sodium chloride and dry over MgSO₄. Remove the solvents (in vacuo) and flash chromatograph the residue from silica gel eluting with 30% EtOAc/hexane to yield 0.5 gm of the desired product, as a viscous oil. Rf is 0.39 (eluting from silica gel with 25% EtOAc/hexane).

Step I: 1,18-Bis(2,3-butadienyl)-1,5,14,18-tetraazaoctadecane•4HCl

Dissolve 0.5 gm of the product of Step H in 2 ml of EtOH and while stirring treat the mixture with 10 ml of 2N HCl in Et₂O. Stir the resulting mixture overnight, filter and dry the solids (in vacuo) to obtain 0.22 gm of the desired product, mp 283°–284° C. dec.

EXAMPLE 10

Potentiation of Natural Cell-Mediated Cytotoxicity by the Compound 3,7,15,19-Tetraazaheneicosane tetrahydrochloride BDFI mice were injected (i.p.) on day zero with $10^5$ L1210. Spleens were aseptically removed, teased apart in complete RPMI-1640, and filtered through sterile gauze to obtain single cell suspensions. Erythrocytes were lysed by suspending cells in buffer (0.155M NH₄Cl, 0.1 mM EDTA, and 0.01M KHCO₃). The spleen cells from 3 mice per experimental group were pooled, washed, and viability determined by trypan blue exclusion. These splenic effector cells were then directly assayed for cytotoxicity against $^{51}$Cr-labeled YAC-1 target cells. The target cells ($10^6$) were labeled with 100 µCi of Na₂$^{51}$CrO₄ at 37° C. for 1 hr. Labeled target cells were then washed (3×) and added in triplicate (104/well) to 96-well round bottom microtiter plates containing different numbers of effector cells to give various effector to target cell ratios in 0.1 ml complete RPMI-1640/well. These plates were then centrifuged at 50×gm for 3 min and incubated at 37 for 4 hr. Following this inclusion period, the plates were centrifuged at 300×gm for 5 min, the supernatant fluids harvested with a supernatant collection system (Skatron, Sterling, Va.), and the released 51Cr was measured in a Beckman Gamma 5500 counter. Supernatant fluids from target cells incubated alone were assayed for spontaneous release and maximum release was determined by adding 1% sodium dodecyl sulfate. Cell-mediated immunity was assessed on day 7 utilizing $^{51}$Cr labeled YAC-1 tumor target cells. Data is expressed as % specific lysis ($\bar{x}$±s.e., n=3). Cytotoxicity, expressed as the percentage of specific lysis, was calculated and plotted as follows:

We claim:

1. A method of potentiating cell-mediated immunity which comprises administering to a patient suffering from a viral disease an effective cell-mediated immunity potentiating amount of a compound of the formula:

or a pharmaceutically acceptable salt thereof, wherein m is an integer 3 to 12, Z is a saturated $C_2$–$C_6$ alkylene moiety of straight or branched chain configuration, each R group is independently H, a $C_1$–$C_6$ saturated or unsaturated hydrocarbyl, or —(CH₂)ₓ—(Ar)—X wherein Ar is phenyl or naphthyl, X is H, $C_1$–$C_6$ alkoxy, halogen, $C_1$–$C_4$ alkyl, or —S(O)ₓR₁, wherein x is an integer 0, 1, or 2, and R₁ is $C_1$–$C_6$ alkyl with the proviso that at least one of R must be other than H.

2. A method of potentiating the activity of effector cells of the cellular immune system which comprises administering to a patient suffering from a viral disease an effective effector cell potentiating amount of a compound of the formula:

or a pharmaceutically acceptable salt thereof, wherein m is an integer 3 to 12, Z is a saturated $C_2$–$C_6$ alkylene moiety of straight or branched chain configuration, each R group is independently H, a $C_1$–$C_6$ saturated or unsaturated hydrocarbyl, or —$(CH_2)_x$—(Ar)—X wherein X is H, $C_1$–$C_6$ alkoxy, halogen, $C_1$–$C_4$ alkyl or —$S(O)_xR_1$, x is an integer 0, 1, or 2, and $R_1$ is $C_1$–$C_6$ alkyl.

3. A method according to claim 2 wherein the effector cell potentiated is a T-cell.

4. A method according to claim 2 wherein the effector cell potentiated is a natural cell-mediated cytotoxic cell.

5. A method according to claim 2 wherein the effector cell potentiated is a macrophage.

6. The method according to claim 1, wherein Z is $C_3$.

7. The method according to claim 6, wherein m is 8.

8. The method according to claim 1, wherein $R_1$ is H, methyl or ethyl.

9. The method according to claim 1, wherein Z is an alkyl-substituted propylene chain.

10. The method according to claim 1, wherein Q is a saturated alkyl moiety comprising 1 to 3 carbon atoms of straight or branched chain configuration.

11. The method according to claim 1, wherein Z is $C_2$.

12. The method according to claim 1, wherein the compound is 1,18-Bis[(phenyl)methyl]-1,5,14,18-tetraazaoctadecane, or a pharmaceutically acceptable salt thereof.

13. The method according to claim 1, wherein the compound is 1,20-Bis[(phenyl)methyl]-1,6,15,20-tetraazaeicosane or a pharmaceutically acceptable salt thereof, or a pharmaceutically acceptable salt thereof.

14. The method according to claim 1, wherein the compound is N,N'-Bis(3-aminobutyl)-1,8-octanediamine, or a pharmaceutically acceptable salt thereof.

15. The method according to claim 1, wherein the compound is N,N'-Bis[(3-ethyolamino)butyl]-1,7-diaminoheptane, or a pharmaceutically acceptable salt thereof.

16. The method according to claim 1, wherein the compound is 1,4,13,16-tetra(t-buyoxycarbonyl)-1,4,13,16-tetraazahexadecane, or a pharmaceutically acceptable salt thereof.

17. The method according to claim 1, wherein the compound as 1,18-Bis[(2-phenyl)ethyl]-1,5,14,18-tetraazaoctadecane, or a pharmaceutically acceptable salt thereof.

18. The method according to claim 1, wherein the compound as 1,18-Bis(phenyl)-1,5,14,18-tetraazaoctadecane, or a pharmaceutically acceptable salt thereof.

19. The method according to claim 1, wherein the compound is 1,18-Bis(2,3-butadienyl)-1,5,14,18-tetraazaoctadecane, or a pharmaceutically acceptable salt thereof.

20. The method according to claim 1, wherein the compound as 3,7,15,19-tetraazaeicosane, or a pharmaceutically acceptable salt thereof.

21. The method according to claim 1, wherein the compound is 3,17-dimethyl-2,6,14,18-tetraazanonadecane, or a pharmaceutically acceptable salt thereof.

22. The method according to claim 1, wherein the compound is 4,6-dimethyl-2,6,14,18-tetraazanonadecane, or a pharmaceutically acceptable salt thereof.

23. The method according to claim 1, wherein the viral disease is caused by an RNA virus or DNA virus.

24. The method according to claim 23, wherein the virus is influenza type A, B or C, mumps, measles, rhinovirus, dengue, rubella, rabies, hepatitis virus A, or encephalitis virus.

25. The method according to claim 23, wherein the virus is human immunodeficiency virus.

26. The method according to claim 23, wherein the virus is HTLV-I, HTLV-II or HTLV-III.

27. The method according to claim 23, wherein the virus is herpes, vaccinia, pappiloma virus or hepatitis virus B.

28. The method according to claim 2, wherein the vital disease is caused by an RNA virus or DNA virus.

29. The method according to claim 28, wherein the virus is influenza type A, B or C, mumps, measles, rhinovirus, dengue, rubella, rabies, hepatitis virus A, or encephalitis virus.

30. The method according to claim 28, wherein the virus is human immunodeficiency virus.

31. The method according to claim 28, wherein the virus is HTLV-I, HTLV-II or HTLV-III.

32. The method according to claim 28, wherein the virus is herpes, vaccinia, pappiloma virus or hepatitis virus B.

* * * * *

UNITED STATES PATENT AND TRADEMARK OFFICE
CERTIFICATE OF CORRECTION

PATENT NO. : 5,719,193

DATED : February 17, 1998

INVENTOR(S) : Terry L. Bowlin

It is certified that error appears in the above-identified patent and that said Letters Patent is hereby corrected as shown below:

Column 1, Line 9 Patent reads "of ser." and should read -- application serial --.
    Line 10 Patent reads "of ser." and should read -- application serial --.

Column 15, Line 15 Patent reads "MgSO4" and should read -- $MgSO_4$ --.

Column 17, Line 44 Patent reads " (methansulfonyl)" and should read -- (Methanesulfonyl) --.

Column 19, Line 38 Patent reads " (t-buyoxycarbonyl)" and should read -- (t-butyoxycarbonyl) --.
    Line 41 Patent reads "as 1, 18-" and should read -- is 1,18 - --.

Column 20, Line 30 Patent reads "vital" and should read -- virus --.

Description of the Drawing Patent reads "Effector: Target Ratio" and should read -- Effector: Target Ratio Figure 1 on bottom of page -- .

Signed and Sealed this

Eleventh Day of July, 2000

Attest:

Attesting Officer

Q. TODD DICKINSON

Director of Patents and Trademarks